(12) United States Patent
Wilmet et al.

(10) Patent No.: US 6,730,817 B1
(45) Date of Patent: May 4, 2004

(54) METHOD FOR PREPARING 1,1,1,3,3-PENTAFLUOROPROPANE

(75) Inventors: Vincent Wilmet, Wavre (BE); Francine Janssens, Vilvoorde (BE); Jean-Paul Schoebrechts, Grez-Doiceau (BE)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 09/051,746

(22) PCT Filed: Oct. 4, 1996

(86) PCT No.: PCT/EP96/04315

§ 371 (c)(1),
(2), (4) Date: Jun. 8, 1998

(87) PCT Pub. No.: WO97/15540

PCT Pub. Date: May 1, 1997

(30) Foreign Application Priority Data

Oct. 23, 1995 (FR) .............................. 95 12558

(51) Int. Cl.[7] .................. C07C 17/00; C07C 17/08; C07C 19/08; C07C 17/266; C07C 21/18
(52) U.S. Cl. ........................ 570/167; 570/172
(58) Field of Search .................. 570/167, 172

(56) References Cited

U.S. PATENT DOCUMENTS 3,862,978 A * 1/1975 Decker et al. .............. 570/172
5,395,997 A * 3/1995 Van Der Puy et al. ..... 570/167
5,574,192 A 11/1996 VanDerPuy et al.

FOREIGN PATENT DOCUMENTS

| AU | 32843/95 | 4/1996 |
|---|---|---|
| EP | 0 522 639 | 1/1993 |
| EP | 0 611 744 | 8/1994 |
| EP | 0 703 205 | 3/1996 |
| EP | 0 729 932 | 9/1996 |
| WO | WO95/04021 | 2/1995 |
| WO | WO95/04022 | 2/1995 |
| WO | WO95/05353 | 2/1995 |
| WO | WO96/01797 | 1/1996 |

OTHER PUBLICATIONS

Kotora, Martin et al., "Addition of tetrachloromethane to halogenated ethenes catalyzed by transition metal complexes", *Journal of Molecular Catalysis*, vol. 77, pp. 51–60 (1992).

* cited by examiner

Primary Examiner—Johann Richter
Assistant Examiner—Elvis O. Price
(74) Attorney, Agent, or Firm—Connolly Bove Lodge & Hutz LLP

(57) ABSTRACT

1,1,1,3,3-Pentafluoropropane is produced by reaction between 1,1,1,3,3-pentachloropropane and hydrogen fluoride in the presence of a hydrofluorination catalyst. The 1,1,1,3,3-pentachloropropane may advantageously be obtained by reaction between vinyl chloride and tetrachloromethane in the presence of a telomerization catalyst and of a nitrile.

22 Claims, No Drawings

METHOD FOR PREPARING 1,1,1,3,3-PENTAFLUOROPROPANE

The present invention relates to a process for the preparation of 1,1,1,3,3-pentafluoropropane (HFC-245fa). It also relates more particularly to a process for the preparation of 1,1,1,3,3-pentafluoropropane from 1,1,1,3,3-pentachloropropane.

1,1,1,3,3-Pentafluoropropane is a possible substitute for wholly or partially halogenated chlorofluoro hydrocarbons (CFCs and HCFCs) suspected of having a detrimental effect on the ozone layer. In particular, it is found to be especially advantageous as a blowing agent for the preparation of expanded polymeric materials.

In application WO 95/05353 it has been proposed to prepare 1,1,1,3,3-pentafluoropropane by reaction between 1,1-dichloro-2,2,2-tri-fluoroethane (HCFC-123) and dichlorodifluoromethane (CFC-12), followed by hydrogenation of the 1,1,1,3,3-pentafluoroprop-2-ene obtained. The yield of the first stage of this known process (synthesis of the 1,1,1,3,3-pentafluoroprop-2-ene intermediate) is, however, very low.

In application WO 95/04022 it has been proposed to prepare 1,1,1,3,3-pentafluoropropane by a three-stage process consisting, in a first stage, in the preparation of 1,1,1,3,3,3-hexachloropropane by reaction between tetrachloromethane and vinylidene chloride, in a second stage in the conversion of the hexachloropropane obtained to 1,1,1,3,3-pentafluoro-3-chloropropane by reaction with hydrogen fluoride and, in a third stage, in the reduction of the pentafluorochloropropane obtained to 1,1,1,3,3-pentafluoropropane by reaction with hydrogen. This process has the disadvantage of giving rise to large quantities of 1,1,1,3,3,3-hexafluoropropane during the second stage.

In application EP-A-611744 it has been proposed to prepare 1,1,1,3,3-pentafluoropropane by reaction between 1,1,1,3,3-pentafluoro-2,3-dichloropropane and hydrogen. The 1,1,1,3,3-pentafluoro-2,3-dichloropropane employed as raw material in this known process is not, however, a common product and cannot be easily prepared.

The objective of the present invention is to provide a process for the preparation of 1,1,1,3,3-pentafluoropropane which does not exhibit the disadvantages of the abovementioned known processes, which uses reactants that are commonly or easily accessible and which has a high yield, thus meeting industrial economic requirements.

The invention consequently relates to a process for the preparation of 1,1,1,3,3-pentafluoropropane, according to which 1,1,1,3,3-pentachloropropane is reacted with hydrogen fluoride in the presence of a hydrofluorination catalyst.

In the process according to the invention the hydrofluorination catalyst is advantageously chosen from the derivatives of metals of groups 3, 4, 5, 13, 14 and 15 of the Periodic Table of the elements (IUPAC 1988) and their mixtures (groups of the Periodic Table of the elements which were previously called IIIA, IVa, IVb, Va, Vb and VIb). The derivatives of the metals are intended to mean the hydroxides, oxides and the organic or inorganic salts of these metals, as well as their mixtures. Those particularly adopted are the titanium, tantalum, molybdenum, boron, tin and antimony derivatives. The catalyst is preferably chosen from the derivatives of metals of groups 14 (IVa) and 15 (Va) of the Periodic Table of the elements, and more particularly from tin and antimony derivatives. In the process according to the invention the preferred derivatives of the metals are the salts and these are preferably chosen from the halides and more particularly from chlorides, fluorides and chlorofluorides. Particularly preferred hydrofluorination catalysts according to the present invention are tin and antimony chlorides, fluorides and chlorofluorides, especially tin tetrachloride and antimony pentachloride. Antimony pentachloride is very particularly recommended.

In the case where the catalyst is selected from metal fluorides and chlorofluorides, these can be obtained from a chloride which is subjected to an at least partial fluorination. This fluorination may, for example, be carried out by means of hydrogen fluoride, before the catalyst is brought into contact with 1,1,1,3,3-pentachloropropane. In an alternative form, it may be carried out in situ, during the reaction of 1,1,1,3,3-pentachlioropropane with hydrogen fluoride.

The quantity of catalyst used can vary within wide limits. It is generally at least 0.001 mole of catalyst per mole of 1,1,1,3,3-pentachloropropane. It is preferably at least 0.01 mole of catalyst per mole of 1,1,1,3,3-pentachloropropane. In principle there is no upper limit to the quantity of catalyst used. For example, in a process carried out continuously in liquid phase, the molar ratio of the catalyst to 1,1,1,3,3-pentachloropropane may reach 1000. In practice, however, at most approximately 5 moles of catalyst are generally employed per mole of 1,1,1,3,3-pentachloropropane. Approximately 1 mole is preferably not exceeded. In a particularly preferred manner, approximately 0.5 moles of catalyst per mole of 1,1,1,3,3-pentachloropropane are generally not exceeded.

The molar ratio of hydrogen fluoride to the 1,1,1,3,3-pentachloropropane used is generally at least 5. The work is preferably done with a molar ratio of at least 8. The molar ratio of hydrogen fluoride to the 1,1,1,3,3-pentachloropropane used generally does not exceed 100. It preferably does not exceed 50.

The temperature at which the hydrofluorination is performed is generally at least 50° C. It is preferably at least 80° C. The temperature generally does not exceed 150° C. It preferably does not exceed 130° C. With antimony pentachloride as catalyst good results are obtained at a temperature of 100 to 120° C.

The process according to the invention is preferably carried out in liquid phase. In this case the pressure is chosen so as to keep the reaction mixture in liquid form. The pressure used varies as a function of the temperature of the reaction mixture. It is generally from 2 bar to 40 bar. The work is preferably carried out at a temperature and pressure at which, furthermore, the 1,1,1,3,3-pentafluoropropane produced is at least partially in gaseous form, which enables it to be easily isolated from the reaction mixture.

The process according to the invention may be carried out continuously or noncontinuously. It is to be understood that, in a noncontinuous process, the quantity of catalyst used is expressed in relation to the initial quantity of 1,1,1,3,3-pentachloropropane used and, in a continuous process, in relation to the stationary quantity of 1,1,1,3,3-pentachloropropane present in the liquid phase.

The residence time of the reactants in the reactor must be sufficient for the reaction of 1,1,1,3,3-pentachloropropane with hydrogen fluoride to take place with an acceptable yield. It can easily be determined as a function of the operating conditions adopted.

The process according to the invention can be carried out in any reactor made of a material that is resistant to the temperature, the pressure and the reactants employed, especially to hydrogen fluoride. It is advantageous to separate the 1,1,1,3,3-pentafluoropropane and the hydrogen chloride from the reaction mixture as they are being formed and to keep in, or return to, the reactor the unconverted reactants, as well as the chlorofluoropropanes possibly formed by incomplete fluorination of 1,1,1,3,3-pentachloropropane. To this end the process according to the invention is advantageously carried out in a reactor equipped with a device for drawing off a gas stream, this device consisting, for example, of a distillation column and a reflux condenser mounted above the reactor. By means of suitable control, this device makes it possible to draw off in vapour phase the 1,1,1,3,3-pentafluoropropane and hydrogen chloride which are produced while keeping in the reactor, in the liquid state, the unconverted 1,1,1,3,3-pentachloropropane and most of the hydrogen fluoride, as well as, where appropriate, most of the products of partial fluorination of 1,1,1,3,3-pentachloropropane.

The 1,1,1,3,3-pentachloropropane used in the process according to the invention can advantageously be obtained by reaction of vinyl chloride with tetrachloromethane, as described, for example, by M. Kotora et al., Journal of Molecular Catalysis, (1992), vol. 77, p. 51–60. It is thus possible to obtain 1,1,1,3,3-pentafluoropropane in two stages from easily accessible materials.

In a preferred alternative form the process according to the invention for the preparation of 1,1,1,3,3-pentafluoropropane includes a telomerization stage in which vinyl chloride and tetrachloromethane are reacted in the presence of a telomerization catalyst, so as to obtain 1,1,1,3,3-pentachloropropane, and the subsequent hydrofluorination stage in which the 1,1,1,3,3-pentachloropropane obtained in the telomerization stage is reacted with hydrogen fluoride in the presence of a hydrofluorination catalyst.

The telomerization catalyst may be chosen from the compounds of metals from groups 8 to 11 of the Periodic Table of the elements (IUPAC 1988) and their mixtures. Compounds of metals of groups 8 and 11 are preferred. Iron and copper compounds are adopted in particular, those of copper being very particularly preferred. Compounds of metals of groups 8 to 11 are intended to mean the organic and inorganic derivatives of these metals and their mixtures. The preferred derivatives are the inorganic salts, the chlorides being particularly preferred. Telomerization catalysts which are particularly preferred according to the present invention are cuprous chloride, cupric chloride and their mixtures. Very good results have been obtained with copper (I) chloride(cuprous chloride).

The quantity of telomerization catalyst used can vary within wide limits. It is generally at least 0.001 mole of catalyst per mole of vinyl chloride. It is preferably at least 0.005 moles of catalyst per mole of vinyl chloride. In a process carried out continuously in liquid phase the molar ratio of the catalyst to vinyl chloride in the reaction mixture can reach 1000. In a process carried out noncontinuously at most approximately 0.5 moles of catalyst are preferably employed, preferably not more than 0.2 moles of catalyst and, in a particularly preferred manner 0.1 mole or less of catalyst per mole of vinyl chloride used.

A cocatalyst can be used in the telomerization stage. Amines can be employed as cocatalyst, preferably in a concentration of 0.1 to 20 moles per mole of telomerization catalyst. Amines which may be mentioned as being usable as cocatalyst in the telomerization stage of the process according to the invention are alkanolamines, alkylamines and aromatic amines, for example ethanolamine, n-butylamine, n-propylamine, isopropylamine, benzylamine and pyridine.

The molar ratio of tetrachloromethane to the vinyl chloride used in the telomerization stage is generally at least 1.5. The work is preferably done with a molar ratio of at least 2. In principle there is no upper limit to the molar ratio of tetrachloromethane to vinyl chloride. For example, in a process carried out continuously in liquid phase, the molar ratio of the stationary quantities of tetrachloromethane and vinyl chloride in the reaction mixture may reach 1000. In a process carried out noncontinuously at most approximately 50 moles, preferably at most 20 moles and, in a particularly preferred manner, at most 10 moles of tetrachloromethane are generally used per mole of vinyl chloride.

The temperature at which the telomerization of vinyl chloride with tetrachloromethane is performed is generally at least 25° C. It is preferably at least 70° C. In general the telomerization temperature does not exceed 200° C. It preferably does not exceed 160° C. With cuprous chloride as catalyst good results have been obtained at a temperature of 100 to 140° C., in particular at a temperature of 110 to 130° C.

The telomerization reaction is generally carried out in liquid phase, advantageously in the presence of a solvent. Solvents that can be employed in the telomerization stage are especially alcohols such as methanol, ethanol, isopropanol and tert-butanol, and nitriles, in particular acetonitrile and propionitrile. Nitriles are preferred. The molar ratio of the solvent to the telomerization catalyst generally does not exceed 1000. Good results have been obtained with a molar ratio of the solvent to the telomerization catalyst of 20 to 400.

In the process according to the invention the presence of a nitrile is particularly advantageous, especially when the telomerization catalyst is a chloride, most especially cuprous chloride. The invention consequently also relates to a process for the preparation of 1,1,1,3,3-pentachloropropane, in which vinyl chloride and tetrachloromethane are reacted in the presence of a chloride of a metal of groups 8 to 11 of the Periodic Table of the elements (IUPAC 1988) and of a nitrile, as defined and in the conditions described above.

The examples hereinafter illustrate the invention without any limitation being implied.

EXAMPLE 1

Preparation of 1,1,1,3,3-pentachloropropane 4.43 moles of acetonitrile, 6.57 moles of tetrachloromethane, 0.11 mole of copper(I) chloride and 2.21 moles of vinyl chloride were introduced into a 1.5 l autoclave lined with a Teflon® fluorocarbon resin, equipped with a mechanical stirrer and a temperature probe. The autoclave was then immersed in a thermostated bath maintained at a temperature of 120° C. for 66 h with continuous stirring. After having reached 8.5 bar the autogenous pressure decreased, reaching 6 bar after 24 hours' reaction and 5.9 bar after 66 hours. The autoclave was then cooled and then the reaction mixture was distilled at reduced pressure. 380 g of 1,1,1,3,3-pentachloropropane were obtained, which represents a yield of 80% relative to the vinyl chloride used.

EXAMPLES 2–3

Preparation of 1,1,1,3,3-pentachloropropane

Acetonitrile (AcN), tetrachloromethane, copper(I) chloride and vinyl chloride (VC) were introduced into the autoclave described in Example I in the proportions reported in Table I. The conditions of reaction under autogenous pressure and the results obtained are also presented in Table 1.

TABLE 1

| Example | 2 | 3 |
|---|---|---|
| VC/CCl$_4$/AcN/CuCl molar ratio | 1/6/2/0.07 | 1/3.1/2.2/0.03 |
| Reaction temperature | 120° C. | 115° C. |
| Reaction period | 36 h | 96 h |
| VC conversion (% of VC used) | 83% | 99% |
| Selectivity for 1,1,1,3,3-pentachloropropane (% of the VC converted transformed into 1,1,1,3,3-pentachloropropane | 91% | 85% |

EXAMPLE 4

Hydrofluorination of 1,1,1,3,3-pentachloropropane 0.21 moles of 1,1,1,3,3-pentachloropropane, 0.076 moles of antimony pentachloride and 10 moles of hydrogen fluoride were introduced into a 0.5 l autoclave made of Hastelloy B2 stainless steel, equipped with a bladed mechanical stirrer, a temperature probe and a dip pipe enabling liquid phase samples to be taken during the test. The autoclave was then immersed in a thermostated bath maintained at a temperature of 120° C. with continuous stirring for 21 hours. The pressure was controlled at 25 bar. A sample taken after 2 hours' reaction showed that more than 99 mol % of the 1,1,1,3,3-pentachloropropane used was already converted, including 66% to 1,1,1,3,3-pentafluoropropane. After 21 hours' reaction virtually all the 1,1,1,3,3-pentachloropropane used was converted, including 92 mol % to 1,1,1,3,3-pentafluoropropane and approximately 6% to intermediate chlorofluoropropanes formed by incomplete fluorination of 1,1,1,3,3-pentachloropropane.

What is claimed is:

1. In a process for the preparation of 1,1,1,3,3-pentafluoropropane comprising reaction of 1,1,1,3,3-pentachloropropane with hydrogen fluoride in the presence of a hydrofluorination catalyst, the improvement which comprises carrying out the reaction at a temperature and under a pressure at which 1,1,1,3,3-pentafluoropropane is gaseous and isolating and 1,1,1,3,3-pentafluoropropane from the reaction mixture by drawing off 1,1,1,3,3-pentafluoropropane and hydrogen chloride in a gaseous phase as each of said 1,1,1,3,3-pentafluoropropane and hydrogen chloride is being formed.

2. The process of claim 1, which comprises conducting the reaction continuously in a liquid phase and maintaining a molar ratio of the catalyst to 1,1,1,3,3-pentachloropropane maintained from 0.001 to 1000.

3. The process of claim 2, wherein the molar ratio of the catalyst to 1,1,1,3,3-pentachloroproprane is greater than 0.5.

4. The process of claim 3 wherein from 5 to 100 moles of hydrogen fluoride are used per mole of 1,1,1,3,3-pentachloroproprane.

5. The process of claim 1 wherein the reaction is carried out at a temperature of approximately 50 to 150° C.

6. The process of claim 1 wherein the 1,1,1,3,3-pentachloroproprane is prepared by reaction between vinyl chloride and tetrachloromethane.

7. The process of claim 1, wherein the hydrofluorination catalyst is selected from the group consisting of derivatives of metals of Groups IIIa, IVa, IVb, Va, Vb and VIb of the periodic table.

8. The process of claim 7, wherein the hydrofluorination catalyst is a derivative of a metal selected from the group consisting of titanium and tin.

9. The process of claim 7, wherein the pentachloropropane is reacted with hydrogen fluoride in the presence of a hydrofluorination catalyst.

10. The process of claim 7, wherein the hydrofluorination catalyst is selected from the group consisting of tin and antimony chlorides, fluorides and chlorofluorides.

11. The process of claim 7, wherein the catalyst is antimony pentachloride.

12. In a process for the preparation of 1,1,1,3,3-pentafluoropropane comprising reaction of 1,1,1,3,3-pentachloropropane with hydrogen fluoride in the presence of a hydrofluorination catalyst, the improvement which comprises carrying out the reaction in a reactor equipped with a device for drawing off a gas stream at a temperature and under a pressure at which 1,1,1,3,3-pentafluoropropane is gaseous and wherein said device is controlled (a) to draw off a gas stream comprising 1,1,1,3,3-pentafluoropropane and hydrogen chloride as each of said 1,1,1,3,3-pentafluoropropane and hydrogen chloride is being formed thereby isolating said 1,1,1,3,3-pentafluoropropane from the reaction mixture (b) to keep in the reactor in the liquid state the unconverted 1,1,1,3,3-pentachloropropane, most of the hydrogen fluoride and most of the products of partial fluorination of 1,1,1,3,3-pentachloropropane.

13. The process of claim 12, which comprises conducting the reaction continuously in a liquid phase and maintaining a molar ratio of the catalyst to 1,1,1,3,3-pentachloropropane maintained from 0.001 to 1000.

14. The process of claim 13, wherein the molar ratio of the catalyst to 1,1,1,3,3-pentachloroproprane is greater than 0.5.

15. The process of claim 12, wherein from 5 to 100 moles of hydrogen fluoride are used per mole of 1,1,1,3,3-pentachloroproprane.

16. The process of claim 12, wherein the reaction is carried out at a temperature of approximately 50 to 150° C.

17. The process of claim 12, wherein the 1,1,1,3,3-pentachloroproprane is prepared by reaction between vinyl chloride and tetrachloromethane.

18. The process of claim 12, wherein the hydrofluorination catalyst is selected from the group consisting of derivatives of metals of Groups IIIa, IVa, IVb, Va, Vb and VIb of the periodic table.

19. The process of claim 18, wherein the hydrofluorination catalyst is a derivative of a metal selected from the group consisting of titanium and tin.

20. The process of claim 18, wherein the pentachloropropane is reacted with hydrogen fluoride in the presence of a hydrofluorination catalyst.

21. The process of claim 18, wherein the hydrofluorination catalyst is selected from the group consisting of tin and antimony chlorides, fluorides and chlorofluorides.

22. The process of claim 18, wherein the catalyst is antimony pentachloride.

* * * * *

UNITED STATES PATENT AND TRADEMARK OFFICE
CERTIFICATE OF CORRECTION

PATENT NO.    : 6,730,817 B1
DATED         : May 4, 2004
INVENTOR(S)   : Wilmet et al.

It is certified that error appears in the above-identified patent and that said Letters Patent is hereby corrected as shown below:

<u>Title page,</u>
Item [*] Notice, should read:
-- Subject to any disclaimer, the term of this patent is extended or
Adjusted under 35 U.S.C. 154(b) by 749 days. --

Signed and Sealed this

Fifteenth Day of June, 2004

JON W. DUDAS
*Acting Director of the United States Patent and Trademark Office*